(12) United States Patent
Deguchi et al.

(10) Patent No.: US 9,551,077 B2
(45) Date of Patent: Jan. 24, 2017

(54) PHOTOELECTRODE USED FOR CARBON DIOXIDE REDUCTION AND METHOD FOR REDUCING CARBON DIOXIDE USING THE PHOTOELECTRODE

(71) Applicant: PANASONIC CORPORATION, Osaka (JP)

(72) Inventors: Masahiro Deguchi, Osaka (JP); Satoshi Yotsuhashi, Osaka (JP); Reiko Taniguchi, Osaka (JP); Hiroshi Hashiba, Osaka (JP); Yuka Yamada, Nara (JP); Kazuhiro Ohkawa, Saitama (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 172 days.

(21) Appl. No.: 14/466,170

(22) Filed: Aug. 22, 2014

(65) Prior Publication Data

US 2014/0360883 A1 Dec. 11, 2014

Related U.S. Application Data

(63) Continuation of application No. PCT/JP2013/004185, filed on Jul. 5, 2013.

(30) Foreign Application Priority Data

Aug. 27, 2012 (JP) .................................. 2012-186194

(51) Int. Cl.
*C25B 11/04* (2006.01)
*B01J 23/08* (2006.01)
(Continued)

(52) U.S. Cl.
CPC .......... *C25B 11/0478* (2013.01); *B01J 23/08* (2013.01); *B01J 23/825* (2013.01); *B01J 27/24* (2013.01);
(Continued)

(58) Field of Classification Search
CPC ............. C25B 3/04; C25B 1/003; C25B 9/08; C25B 11/0478; C25B 11/0405; B01J 35/004; B01J 23/08; B01J 27/24; B01J 23/825; C07C 1/12; C07C 27/04; C07C 51/00
(Continued)

(56) References Cited

U.S. PATENT DOCUMENTS 8,652,989 B2 2/2014 Sato et al.
8,696,883 B2 4/2014 Yotsuhashi et al.
(Continued)

FOREIGN PATENT DOCUMENTS

JP 55-105625 A 8/1980
JP 05-311476 A 11/1993
(Continued)

OTHER PUBLICATIONS

Fujii et al, "Band-Edge Energies and Photoelectrochemical Properties of n-Type AlxGa1—xN and InyGa1—yN Alloys," J. of the Electrochem. Soc. vol. 154, No. 2, pp. B175-B179 (2007).*
(Continued)

*Primary Examiner* — Keith Hendricks
*Assistant Examiner* — Colleen M Raphael
(74) *Attorney, Agent, or Firm* — McDermott Will & Emery LLP (57) ABSTRACT

Disclosed is an anode electrode including a nitride semiconductor layer. This nitride semiconductor layer includes an $Al_xGa_{1-x}N$ layer ($0<x\leq0.25$), an $Al_yGa_{1-y}N$ layer ($0\leq y\leq x$), and a GaN layer. The $Al_yGa_{1-y}N$ layer is interposed between
(Continued)

the $Al_xGa_{1-x}N$ layer and the GaN layer. The value of x is fixed in the thickness direction of the $Al_xGa_{1-x}N$ layer. The value of y decreases from the interface with the $Al_xGa_{1-x}N$ layer f toward the interface with the GaN layer. The $Al_xGa_{1-x}N$ layer is irradiated with light having a wavelength of 360 nm or less so as to reduce carbon dioxide.

14 Claims, 4 Drawing Sheets

(51) Int. Cl.
- B01J 27/24 (2006.01)
- B01J 35/00 (2006.01)
- C07C 1/12 (2006.01)
- C07C 27/04 (2006.01)
- C07C 51/00 (2006.01)
- C25B 1/00 (2006.01)
- C25B 3/04 (2006.01)
- B01J 23/825 (2006.01)

(52) U.S. Cl.
CPC ............. B01J 35/004 (2013.01); C07C 1/12 (2013.01); C07C 27/04 (2013.01); C07C 51/00 (2013.01); C25B 1/003 (2013.01); C25B 3/04 (2013.01); C25B 11/0405 (2013.01)

(58) Field of Classification Search
USPC .................. 205/340; 204/242; 422/186–187
See application file for complete search history.

(56) References Cited

U.S. PATENT DOCUMENTS

| | | | | |
|---|---|---|---|---|
| 8,709,227 B2 * | 4/2014 | Deguchi | ................. | C25B 1/003 205/340 |
| 8,709,228 B2 * | 4/2014 | Deguchi | ................. | C25B 1/003 205/340 |
| 8,758,578 B2 * | 6/2014 | Nomura | ................. | C25B 1/003 204/242 |
| 9,157,158 B2 * | 10/2015 | Deguchi | ................. | C25B 1/003 |
| 2012/0186644 A1 * | 7/2012 | Ko | ................. | H01G 9/2031 977/773 |
| 2013/0032821 A1 * | 2/2013 | Lee | ................. | H01L 29/66143 257/77 |
| 2013/0062216 A1 * | 3/2013 | Yotsuhashi | ............. | C25B 1/003 205/340 |
| 2013/0105306 A1 * | 5/2013 | Sonoda | ................. | C25B 1/003 204/242 |

FOREIGN PATENT DOCUMENTS

| | | |
|---|---|---|
| JP | 06-126189 A | 5/1994 |
| JP | 07-188961 A | 7/1995 |
| JP | 2526396 B2 | 8/1996 |
| JP | 2003-275599 A | 9/2003 |
| JP | 2004-059507 A | 2/2004 |
| JP | 3876305 B2 | 1/2007 |
| JP | 4158850 B2 | 10/2008 |
| JP | 2010-064066 A | 3/2010 |
| JP | 2011-094194 A | 5/2011 |
| WO | 2006-082801 A1 | 8/2006 |
| WO | 2012-046374 A1 | 4/2012 |

OTHER PUBLICATIONS

Yotsuhashi, Satoshi, et al.: "Enhanced CO2 reduction capability in an AlGaN/GaN photoelectrode", Applied Physics Letters, vol. 100, No. 24, pp. 243904-1-243904-3, 2012.

International Search Report issued in PCT/JP2013/004185, dated Aug. 27, 2013, with English translation.

* cited by examiner

PHOTOELECTRODE USED FOR CARBON DIOXIDE REDUCTION AND METHOD FOR REDUCING CARBON DIOXIDE USING THE PHOTOELECTRODE

This is a continuation of International Application No. PCT/JP2013/004185, with an international filing date of Jul. 5, 2013, which claims the foreign priority of Japanese Patent Application No. 2012-186194, filed on Aug. 27, 2012, the entire contents of both of which are hereby incorporated by reference.

BACKGROUND OF THE INVENTION

1. Technical Field of the Invention

The present disclosure relates to a photoelectrode used to reduce carbon dioxide by light energy, and to a method for reducing carbon dioxide using the photoelectrode.

2. Description of Related Art

JP 55(1980)-105625 A, JP 2526396 B2, JP 3876305 B2, JP 4158850 B2, JP 2010-064066 A, JP 2011-094194 A, JP 05(1993)-311476 A, JP 07(1995)-188961 A, and WO 2012/046374 A1 each disclose a method for reducing carbon dioxide by light energy.

JP 55(1980)-105625 A and JP 2526396 B2 each disclose a method for reducing carbon dioxide using an oxide semiconductor such as titanium oxide (titania, $TiO_2$) as a photocatalytic material.

JP 3876305 B2, JP 4158850 B2, and JP 2010-064066 A each disclose a technique for reducing carbon dioxide using a composite photocatalytic material including a specific metal and a semiconductor.

JP 2011-094194 A discloses a method for reducing carbon dioxide using a photoelectrode (anode electrode) made of a photocatalytic material containing a semiconductor and a cathode electrode for carbon dioxide reduction made of a photocatalytic material containing a metal complex.

JP 05(1993)-311476 A and JP 07(1995)-188961 A each disclose a method for reducing carbon dioxide using a $TiO_2$ photoelectrode as a photoelectrode (anode electrode) for producing oxygen from water. In this method, light irradiation of the photoelectrode and input from an external power source such as a solar cell or a potentiostat are utilized in combination to reduce carbon dioxide.

WO 2012/046374 A1 discloses a method for reducing carbon dioxide using a semiconductor photoelectrode containing gallium nitride (GaN) as a photoelectrode (anode electrode). In this method, light irradiation of the photoelectrode is utilized alone to reduce carbon dioxide.

SUMMARY OF THE INVENTION

One non-limiting and exemplary embodiment provides a novel photoelectrode used to reduce the loss of photoexcited carriers and thus to reduce carbon dioxide efficiently. This photoelectrode is used in a novel method for reducing carbon dioxide by light energy alone and without using an external power source.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature a photoelectrode used to reduce carbon dioxide by light energy.

This photoelectrode includes a region including a nitride semiconductor layer in which a first aluminum gallium nitride layer (composition formula: $Al_xGa_{1-x}N$, where a value of x representing a composition ratio of Al is a fixed value that satisfies $0<x\leq0.25$), a second aluminum gallium nitride layer (composition formula: $Al_yGa_{1-y}N$, where a value of y representing a composition ratio of Al is a variable value that satisfies $0\leq y\leq x$), and a gallium nitride layer (composition formula: GaN) are laminated in this order from a surface of the photoelectrode to be irradiated with light. In this photoelectrode, the value of y in the second aluminum gallium nitride layer changes, without any increase, from an interface with the first aluminum gallium nitride layer toward an interface with the gallium nitride layer.

In another general aspect, the techniques disclosed here feature a method for reducing carbon dioxide by light energy.

This method includes the steps of:

(a) preparing a carbon dioxide reduction device including a cathode chamber, an anode chamber, a proton conducting membrane, a cathode electrode, and an anode electrode, wherein the anode electrode is a photoelectrode including the region including the nitride semiconductor layer, a first electrolytic solution is contained in the cathode chamber, a second electrolytic solution is contained in the anode chamber, the cathode electrode is in contact with the first electrolytic solution, the anode electrode is in contact with the second electrolytic solution, the proton conducting membrane is interposed between the cathode chamber and the anode chamber, the first electrolytic solution contains carbon dioxide, the cathode electrode is electrically connected to the anode electrode, and a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution.

It should be noted that general or specific embodiments may be implemented as a device, a system, a method, or any elective combination thereof.

The present disclosure is a novel photoelectrode used to reduce carbon dioxide by light energy alone and without using an external power source connected between a cathode electrode and an anode electrode. This photoelectrode reduces the loss of excited carriers and improves the carbon dioxide reduction efficiency. The present disclosure also provides a novel method for reducing carbon dioxide by light energy.

DETAILED DESCRIPTION

<Findings Underlying the Present Disclosure>

First, the findings underlying the present disclosure are described.

In the methods disclosed in JP 55(1980)-105625 A, JP 2526396 B2, JP 3876305 B2, JP 4158850 B2, and JP 2010-064066 A, both water oxidation reaction and carbon dioxide reduction reaction are performed simultaneously with the use of photocatalytic materials alone. However, the carrier excitation region and the reaction region are not separated, and therefore it is difficult to prevent recombination of the carriers generated by light absorption so as to use the carriers efficiently.

In the method disclosed in JP 2011-094194 A, the carrier excitation region (anode electrode) and the reaction region (cathode electrode) are separated to remedy the above problem, but this method requires light irradiation of not only the photoelectrode (anode electrode) for water oxidation but also the cathode electrode for carbon dioxide reduction.

In the methods disclosed in JP 05(1993)-311476 A and JP 07(1995)-188961 A, carbon dioxide is reduced using an anode electrode and a cathode electrode, as in the method disclosed in JP 2011-094194 A, but these methods require an external power source such as a solar cell or a potentiostat in addition to the cathode electrode and the anode electrode.

In the method disclosed in WO2012/046374 A1, carbon dioxide is reduced at the cathode electrode by light irradiation of the gallium nitride photoelectrode (anode electrode) alone. However, since this method has no structure for reducing the loss of the photoexcited carriers in the anode electrode and supplying the carriers to the cathode electrode efficiently, the supply of the carriers from the anode electrode to the cathode electrode limits the rate of carbon dioxide reduction, resulting in a decrease in the efficiency of carbon dioxide reduction.

The patent documents described above report that carbon dioxide can be reduced by light irradiation of a photocatalytic material or a photoelectrode (anode electrode). These documents disclose that organic compounds such as formic acid and hydrocarbon can be produced from carbon dioxide by the use of carriers (electrons and holes) generated by light irradiation for the reactions.

In this light-driven carbon dioxide reduction reaction, the amount of reaction products obtained from carbon dioxide depends on the amount of carriers generated by photoexcitation. Therefore, in order to increase the reaction efficiency, it is necessary to inhibit the recombination of the excited carriers and to reduce the loss of the excited carriers consumed for the production of hydrogen ($H_2$), etc. at the photoelectrode (anode electrode). However, there has been no report of a structure for reducing the loss of carriers excited in the anode electrode, resulting in a decrease in the amount of carriers supplied from the anode electrode to the cathode electrode, which may be problematic.

The present inventors have found that the use of an optimally structured nitride semiconductor layer in a photoelectrode (anode electrode) reduces the loss (consumption) of carriers at the anode electrode and increases the efficiency of carbon dioxide reduction by light energy. The present disclosure has been accomplished based on these findings.

<Description of Aspects of the Present Disclosure>

Next, the aspects of the present disclosure are described.

The first aspect of the present disclosure provides a photoelectrode used for carbon dioxide reduction as described below.

This photoelectrode is used to reduce carbon dioxide by light energy.

This photoelectrode includes a region including a nitride semiconductor layer in which a first aluminum gallium nitride layer (composition formula: $Al_xGa_{1-x}N$, where a value of x representing a composition ratio of Al is a fixed value that satisfies $0 < x \le 0.25$), a second aluminum gallium nitride layer (composition formula: $Al_yGa_{1-y}N$, where a value of y representing a composition ratio of Al is a variable value that satisfies $0 \le y \le x$), and a gallium nitride layer (composition formula: GaN) are laminated in this order from a surface of the photoelectrode to be irradiated with light. In this photoelectrode, the value of y in the second aluminum gallium nitride layer changes, without any increase, from an interface with the first aluminum gallium nitride layer toward an interface with the gallium nitride layer.

According to this aspect, it is possible not only to reduce carbon dioxide by light irradiation of the photoelectrode alone but also to reduce carbon dioxide efficiently because the loss of carriers at the photoelectrode (at the anode electrode) is reduced.

The second aspect of the present disclosure provides the photoelectrode according to the first aspect, wherein the value of x in the first aluminum gallium nitride layer of the photoelectrode may be in a range of $0.05 \le x \le 0.15$.

According to this aspect, the photoelectrode can absorb a wider range of wavelengths of light. Thus, the light irradiated to the photoelectrode can be used effectively.

The third aspect of the present disclosure provides the photoelectrode according to the first or the second aspect, wherein the gallium nitride layer of the photoelectrode may be n-type or $n^+$-type.

According to this aspect, the electrical resistance in the gallium nitride layer is reduced. Thus, the performance of the photoelectrode can be enhanced.

The fourth aspect of the present disclosure provides the photoelectrode according to any one of the first to third aspects, wherein an entire surface or a part of the surface of the first aluminum gallium nitride layer of the photoelectrode may be coated with at least nickel oxide.

According to this aspect, it is possible to increase the oxygen production efficiency at the photoelectrode by the so-called co-catalytic activity of nickel oxide.

The fifth aspect of the present disclosure provides the photoelectrode according to the fourth aspect, wherein the nickel oxide may be in the form of fine particles.

According to this aspect, it is possible to coat the entire surface or a part of the surface of the first aluminum gallium nitride layer of the photoelectrode with nickel oxide with ease and high controllability.

The sixth aspect of the present disclosure provides a method for reducing carbon dioxide by light energy.

This method includes the steps of:

(a) preparing a carbon dioxide reduction device including a cathode chamber, an anode chamber, a proton conducting membrane, a cathode electrode, and an anode electrode, wherein the anode electrode is a photoelectrode including the region including the nitride semiconductor layer according to the first aspect, a first electrolytic solution is contained in the cathode chamber, a second electrolytic solution is contained in the anode chamber, the cathode electrode is in contact with the first electrolytic solution, the anode electrode is in contact with the second electrolytic solution, the proton conducting membrane is interposed between the cathode chamber and the anode chamber, the first electrolytic solution contains carbon dioxide, the cathode electrode is electrically connected to the anode electrode, and a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution.

According to this aspect, it is possible to provide a novel method for reducing carbon dioxide by light irradiation of the photoelectrode alone through more simple and efficient carbon dioxide reduction reaction.

The seventh aspect of the present disclosure provides the method according to the sixth aspect, wherein the cathode electrode may be a metal electrode.

According to this aspect, it is possible to increase the reaction rate and to control carbon dioxide reduction products by selecting an appropriate material for the metal electrode for reducing carbon dioxide.

The eighth aspect of the present disclosure provides the method according to the seventh aspect, wherein the metal electrode (cathode electrode) may contain copper or a copper compound.

According to this aspect, it is possible to produce hydrocarbons such as ethylene ($C_2H_4$) and alcohol components such as ethanol ($C_2H_5OH$) as the carbon dioxide reduction products.

The ninth aspect of the present disclosure provides the method according to the seventh aspect, wherein the metal electrode (cathode electrode) may contain indium or an indium compound.

According to this aspect, it is possible to produce a formic acid (HCOOH) component as a carbon dioxide reduction product with high efficiency.

The tenth aspect of the present disclosure provides the method according to any one of the sixth to ninth aspects, wherein the first electrolytic solution may be an aqueous potassium bicarbonate solution (aqueous $KHCO_3$ solution).

The solution according to this aspect is easy to handle as an electrolytic solution to be contained in the cathode chamber and desirable as an electrolytic solution used for carbon dioxide reduction by light energy.

The eleventh aspect of the present disclosure provides the method according to any one of the sixth to ninth aspects, wherein the first electrolytic solution may be an aqueous potassium chloride solution (aqueous KCl solution) or an aqueous sodium chloride solution (aqueous NaCl solution).

The solution according to this aspect is easy to handle as an electrolytic solution to be contained in the cathode chamber and makes it possible to increase the proportion of hydrocarbons and alcohol components in the carbon dioxide reduction products.

The twelfth aspect of the present disclosure provides the method according to any one of the sixth to eleventh aspects, wherein the second electrolytic solution may be an aqueous sodium hydroxide solution (aqueous NaOH solution).

The solution according to this aspect is easy to handle as an electrolytic solution to be contained in the anode chamber and desirable as an electrolytic solution used for carbon dioxide reduction by light energy.

The thirteenth aspect of the present disclosure provides the method according to any one of the sixth to twelfth aspects, wherein in the step (b), the carbon dioxide reduction device may be placed at room temperature and under atmospheric pressure.

According to this aspect, there is no need to place the carbon dioxide reduction device in a specific environment to reduce carbon dioxide by light energy.

The fourteenth aspect of the present disclosure provides the method according to any one of the sixth to thirteenth aspects, wherein in the step (b), at least one of alcohol, aldehyde, formic acid, carbon monoxide, and hydrocarbon may be obtained from the carbon dioxide.

According to this aspect, it is possible not only to immobilize carbon dioxide but also to obtain a variety of useful substances through carbon dioxide reduction reaction driven by light energy.

Hereinafter, the embodiments of the present disclosure are described in detail. The following description relates to exemplary embodiments of the present disclosure, and the present disclosure is not limited to these embodiments.

(Photoelectrode (Anode Electrode) for Carbon Dioxide Reduction)

Figure 1A:
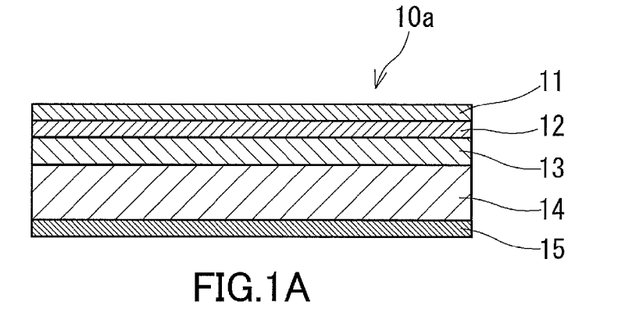
FIG. 1A to FIG. 1D are each a schematic view showing an example of the structure of a photoelectrode (anode electrode) used for carbon dioxide reduction according to the present disclosure.

FIG. 1A to FIG. 1D are each a schematic view showing an example of the structure of a photoelectrode (anode electrode) used for carbon dioxide reduction according to the present disclosure. FIG. 1A is a diagram showing the basic configuration of the photoelectrode of the present disclosure. This photoelectrode 10a includes a first aluminum gallium nitride layer 11 (composition formula: $Al_xGa_{1-x}N$, where a value of x representing a composition ratio of Al is a fixed value that satisfies $0<x\leq 0.25$) to be irradiated with light, a second aluminum gallium nitride layer 12 (composition formula: $Al_yGa_{1-y}N$, where a value of y representing a composition ratio of Al is a variable value that satisfies $0\leq y\leq x$), a gallium nitride layer 13 (composition formula: GaN), an electrically conductive substrate 14 used to form a nitride semiconductor layer (including the layers 11, 12, and 13), and an electrode layer 15 for electrically connecting the photoelectrode 10a to a cathode electrode.

It is generally an effective method for fabricating this photoelectrode 10a to form a thin film of the nitride semiconductor layer (the first aluminum gallium nitride layer 11, the second aluminum gallium nitride layer 12, and the gallium nitride layer 13) on the conductive substrate 14, and the method is not particularly limited as long as such a thin nitride semiconductor film can be formed on a substrate. For example, the method is metal-organic vapor-phase epitaxy. The conductive substrate 14 is not particularly limited. Specific examples of the conductive substrate 14 include a single-crystalline gallium nitride (GaN) substrate and a single-crystalline silicon (Si) substrate having low electrical resistance. The method for forming the electrode layer 15 on the conductive substrate 14 is also not be particularly limited, but the method is desirably vacuum deposition (such as resistance heating evaporation or electron beam evaporation) as a commonly used technique for forming a metal thin film. In the case where an electrically insulating substrate is used, for example, in the case where a sapphire substrate or a high-resistance silicon substrate is used, the nitride semiconductor layer may be formed by the same technique, but it is desirable to configure the anode electrode as shown in FIG. 2A to FIG. 2D below.

The first function of the photoelectrode 10a is to allow the region including the first aluminum gallium nitride layer 11 to absorb light so as to generate photoexcited carriers (electrons and holes) therein and to contribute to oxidation-reduction reactions through the activity of the carriers. Specifically, upon photoexcitation, the holes generated in the first aluminum gallium nitride layer 11 move to the surface of the photoelectrode (the surface of the first aluminum gallium nitride layer) and oxidizes water in contact with the photoelectrode 10a to produce oxygen. That is, the photoelectrode 10a itself serves as an oxygen producing electrode.

Since the band gap of the first aluminum gallium nitride layer 11 of the photoelectrode 10a is 3.4 eV or more, the photoelectrode 10a cannot serve as a light-driven photoelectrode unless it is irradiated with light having a wavelength of at least 360 nm or less. Therefore, for the effective use of light, the composition ratio of aluminum (the value of x) in the first aluminum gallium nitride layer 11 (composition formula: $Al_xGa_{1-x}N$) of the photoelectrode 10a is desirably in a range of $0<x \leq 0.25$, and particularly desirably in a range of $0.05 \leq x \leq 0.15$.

When the first aluminum gallium nitride layer 11 is irradiated with light having wavelengths in the above range, the absorption region of the first aluminum gallium nitride layer 11 has a depth of about 100 nm from the irradiated surface, although it depends on the band gap. Therefore, the thickness of the first aluminum gallium nitride layer 11 is desirably 70 nm or more and 1000 nm or less, and further desirably 80 nm or more and 200 nm or less.

On the other hand, the electrons generated in the first aluminum gallium nitride layer 11 by photoexcitation are collected in the electrode layer 15 disposed in the photoelectrode 10a through the second aluminum gallium nitride layer 12 and the gallium nitride layer 13, and supplied to the cathode electrode for reducing carbon dioxide through a wire (conducting wire) that is electrically connected to the anode electrode and the cathode electrode. In this case, if the consumption of the carriers in the photoelectrode 10a (anode electrode) can be reduced, the efficiency of carbon dioxide reduction can be increased.

In view of this, the second function of this photoelectrode 10a is to transport the photoexcited electrons in the first aluminum gallium nitride layer efficiently to the gallium nitride layer without being consumed in the anode electrode, through a region consisting of the second aluminum gallium nitride layer 12 interposed between the first aluminum gallium nitride layer 11 and the gallium nitride layer 13.

Specifically, the second function of the photoelectrode 10a is to provide a potential difference for the carriers by changing, without any increase, the composition ratio of Al (the value of y) in the second aluminum gallium nitride layer 12 (composition formula: $Al_yGa_{1-y}N$, where the value of y representing the composition ratio of Al is a variable value that satisfies $0 \leq y \leq x$) from the interface with the first aluminum gallium nitride layer 11 toward the interface with the gallium nitride layer 13, so as to efficiently supply the electrons deep into the photoelectrode. If the photoelectrode 10a does not include the second aluminum gallium nitride layer 12 structured as described above, it cannot allow the force for transporting the electrons into the photoelectrode itself to act. Therefore, on the surface layer of the photoelectrode 10a, some of the photoexcited electrons reduce water in contact therewith to produce hydrogen ($H_2$). That is, some of the carriers generated by photoexcitation are consumed for production of hydrogen. Thus, the second aluminum gallium nitride layer 12, in which the composition ratio of Al (the value of y) changes, serves to suppress the production of hydrogen at the anode electrode. How the composition ratio of Al is changed is specifically described below.

The composition ratio of Al (the value of y) in the second aluminum gallium nitride layer 12 (composition formula: $Al_yGa_{1-y}N$) having the above-mentioned functions is a variable value that satisfies $0 \leq y \leq x$. The thickness of the second aluminum gallium nitride layer is desirably 50 nm or more and 500 nm or less, and more desirably 50 nm or more and 100 nm or less.

The concentration of the carriers contained in the first aluminum gallium nitride layer and the second aluminum gallium nitride layer is about $1 \times 10^{16}$ to $1 \times 10^{18}/cm^3$ (carriers per cubic centimeter), and desirably $1 \times 10^{17}/cm^3$ to $3 \times 10^{17}/cm^3$.

In order to efficiently collect the carriers (electrons) generated by light irradiation of the photoelectrode 10a in the electrode layer 15, the first aluminum gallium nitride layer 11 and the second aluminum gallium nitride layer 12 are laminated on the gallium nitride layer 13. Desirably, the gallium nitride layer 13 is n-type or $n^+$-type. Since the n-type or $n^+$-type gallium nitride layer 13 has a reduced electrical resistance, it is effective in reducing the ohmic loss associated with the carrier transport. In this configuration, it is desirable to use a gallium nitride layer doped with an impurity element (such as silicon) and having a low electrical resistance. This configuration was mainly adopted in the following examples. The carrier concentration in this silicon-doped n-type gallium nitride layer is desirably $1 \times 10^{18}/cm^3$ or more, and more desirably about $2 \times 10^{18}/cm^3$ to $8 \times 10^{18}/cm^3$.

Figure 1B:
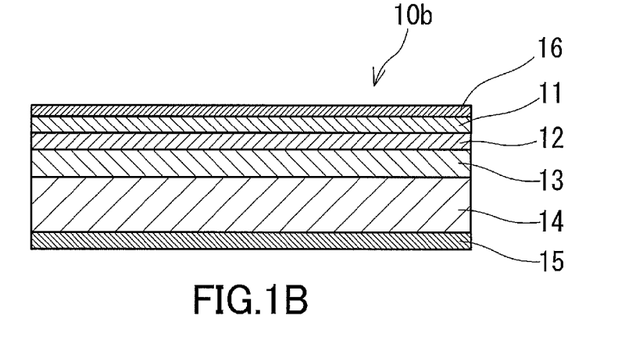

The main configuration of the photoelectrode used for carbon dioxide reduction according to the present embodiment has been described so far. In order to increase the efficiency of oxygen production as the function of the photoelectrode and to increase the durability of the photoelectrode, it is also possible to adopt a configuration as shown in FIG. 1B, in which a surface coating layer 16 containing nickel oxide is disposed on the first aluminum gallium nitride layer 11 without blocking the light irradiation of the first aluminum gallium nitride layer 11. This configuration is obtained by using the surface coating layer 16 having a thickness thin enough (for example, 10 nm or less) not to block the light irradiation or having a band gap large enough to reduce absorption of the light.

Figure 1C:
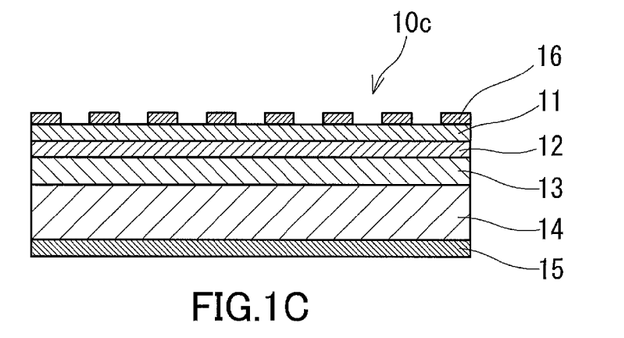
Figure 1D:
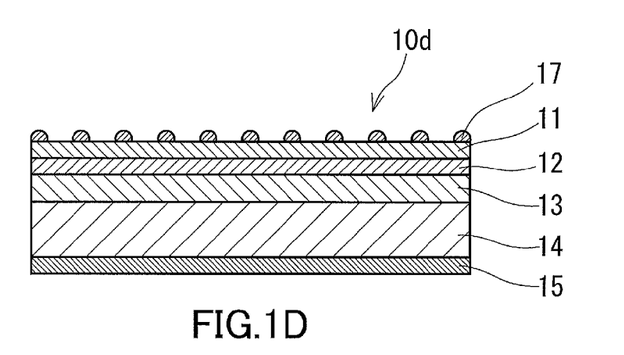

It is also desirable to cut the surface coating layer 16 into pieces and arrange the pieces on the first aluminum gallium nitride layer 11 such that part of the surface of the first aluminum gallium nitride layer 11 is exposed, as shown in FIG. 1C. In this case, the pieces of the surface coating layer 16 do not necessarily have to have a uniform shape, and the pieces of various shapes and sizes may be arranged in a randomly distributed manner on the surface of the first aluminum gallium nitride layer. Furthermore, it is also desirable to provide a configuration as shown in FIG. 1D, in which a large number of nickel oxide fine particles 17 are arranged in a distributed manner on the surface of the first aluminum gallium nitride layer 11.

The present inventors have confirmed that in these configurations, the so-called co-catalytic activity of nickel oxide is effective in increasing the oxygen production efficiency at the photoelectrode.

FIG. 2A to FIG. 2D are each a schematic configuration view of a photoelectrode used for carbon dioxide reduction in which a substrate made of an electrically insulating material (insulating substrate 24) is used instead of the conductive substrate in each of the configurations as shown in FIG. 1A to FIG. 1D. In each of photoelectrodes 20a, 20b, 20c, and 20d shown in FIG. 2A to FIG. 2D, a gallium nitride layer 23 is formed on the insulating substrate 24, a second aluminum gallium nitride layer 22 is formed on the gallium nitride layer 23, and a first aluminum gallium nitride layer 21 is formed on the second aluminum gallium nitride layer 22. In addition, each of the photoelectrodes 20a to 20d includes an electrode layer 25 on the gallium nitride layer 23 formed on the insulating substrate 24. Specific examples of the insulating substrate 24 include a single-crystalline sapphire substrate. The gallium nitride layer 23 has the same structure as the gallium nitride layer 13 described above, and the first aluminum gallium nitride layer 21 and the second aluminum gallium nitride layer 22 also have the same structures as the first aluminum gallium nitride layer 11 and the second aluminum gallium nitride layer 12 described above. Furthermore, in each of the photoelectrodes 20b to 20d shown in FIG. 2B to FIG. 2D, a surface coating layer 26 (or nickel oxide fine particles 27) is (are) disposed on the first aluminum gallium nitride layer 21. This surface coating layer 26 also has the same structure as the surface coating layer 16 described above. Not only the use of any of the configurations shown in FIG. 1A to FIG. 1D but also the use of any of the configurations shown in FIG. 2A to FIG. 2D makes it possible to form a desired photoelectrode used for carbon dioxide reduction.

Figure 3A:
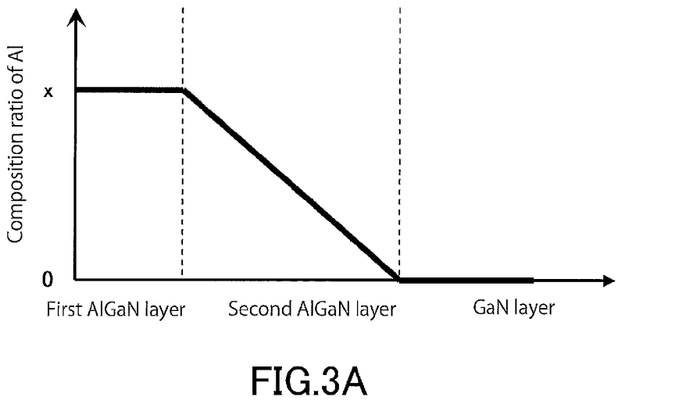
FIG. 3A to FIG. 3C are each a schematic diagram showing an example of the distribution of the composition ratio of aluminum in a second aluminum gallium nitride layer (composition formula: $Al_yGa_{1-y}N$, where the value of y representing the composition ratio of Al is a variable value that satisfies 0≤y≤x) of the photoelectrode used for carbon dioxide reduction of the present disclosure.
Figure 3B:
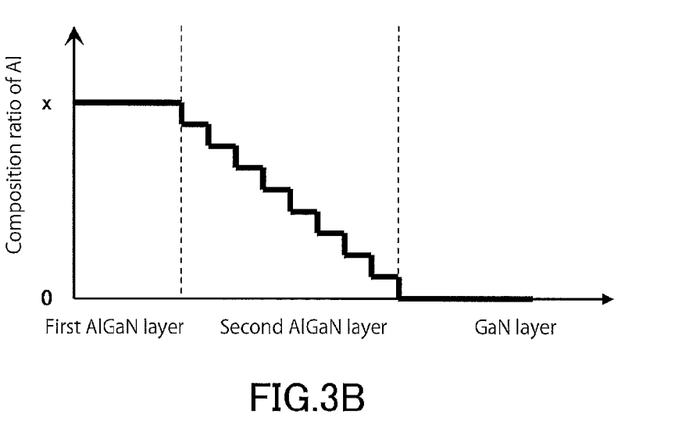
Figure 3C:
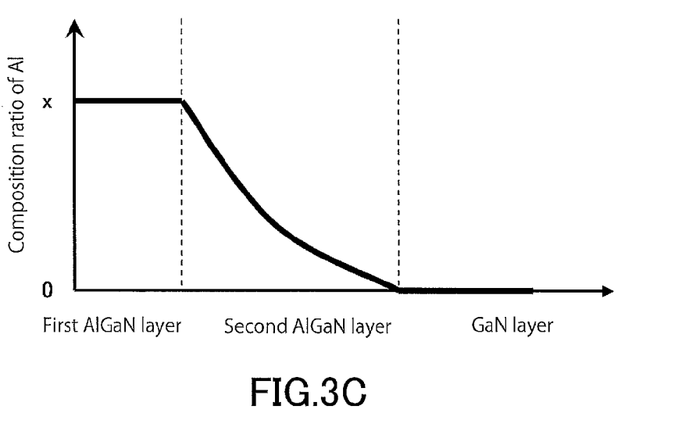

FIG. 3A to FIG. 3C are each a diagram showing an example of the distribution of the composition ratio of aluminum (the value of y) in the second aluminum gallium nitride layer (composition formula: $Al_yGa_{1-y}N$, where the value of y representing the composition ratio of Al is a variable value that satisfies $0 \leq y \leq x$) of the photoelectrode of the present disclosure. It is only necessary that the composition ratio of Al (the value of y) in the second aluminum gallium nitride layer change, without any increase from the composition ratio of Al (the value of x) in the first aluminum gallium nitride layer toward the gallium nitride layer. For example, a structure in which the value of y decreases linearly, that is, the value of y decreases continuously from the value of x to 0, as shown in FIG. 3A, is the best example of the change in the value of y. Alternatively, the value of y does not have to decrease continuously but may decrease step by step (for example, with a relatively small depth (thickness) of 5 to 10 nm per step), as shown in FIG. 3B. Furthermore, a structure in which the rate of change in the composition ratio of Al (differential value) is not constant, as shown in FIG. 3C, can also be adopted.

As described above, the second aluminum gallium nitride layer of the present disclosure may be structured such that the composition ratio of Al in the second aluminum gallium nitride layer changes, without any increase, from the interface with the first aluminum gallium nitride layer toward the interface with the gallium nitride layer.

(Device for Reducing Carbon Dioxide by Light Energy)

Figure 4:
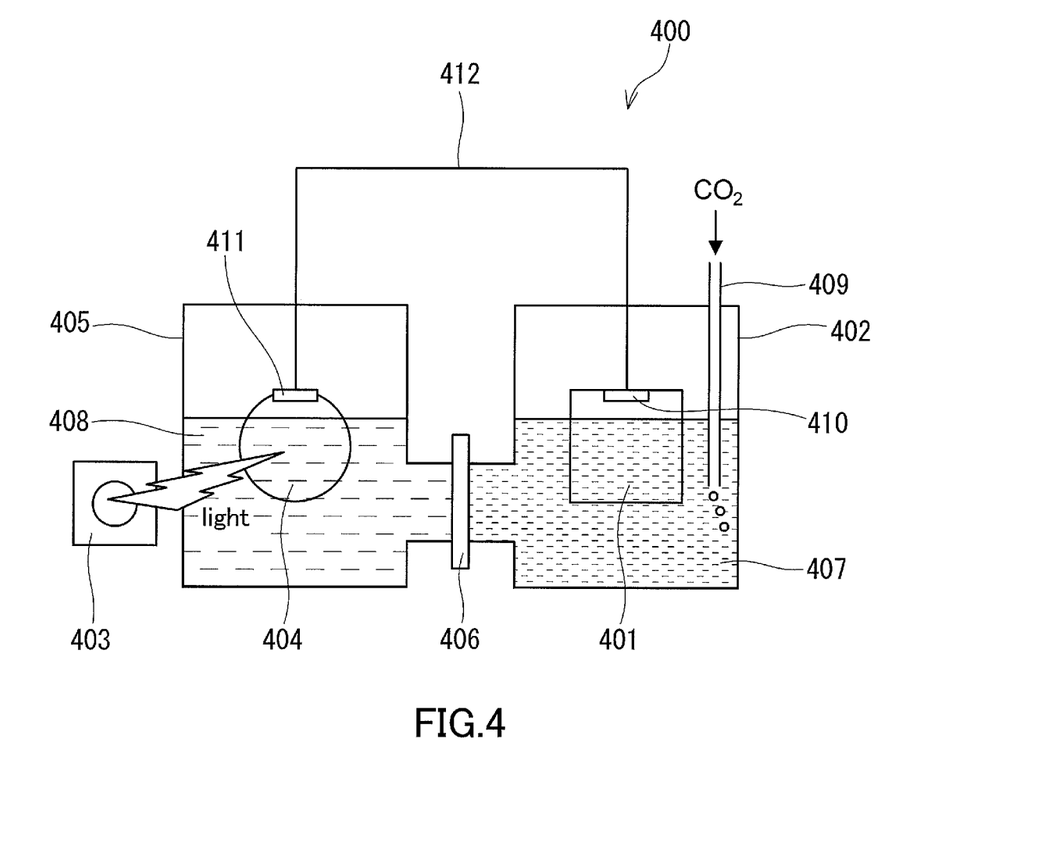
FIG. 4 is a schematic view of a device for reducing carbon dioxide by light energy alone according to an embodiment of the present disclosure.

FIG. 4 shows a schematic view of an example of a device for reducing carbon dioxide by light energy. A device 400 includes a cathode chamber 402, an anode chamber 405, and a proton conducting membrane 406.

A first electrolytic solution 407 is contained in the cathode chamber 402, and the cathode chamber 402 contains a cathode electrode 401. The cathode electrode 401 is in contact with the first electrolytic solution 407. Specifically, the cathode electrode 401 is immersed in the first electrolytic solution 407.

A commonly available electrolytic solution can be used as the first electrolytic solution 407 contained in the cathode chamber 402, but it is particularly desirable to use an aqueous potassium bicarbonate solution (aqueous $KHCO_3$ solution), an aqueous potassium chloride solution (aqueous KCl solution), or an aqueous sodium chloride solution (aqueous NaCl solution). In any of these cases, the concentration of the first electrolytic solution is desirably 1 mol/L or more, and particularly desirably 3 mol/L or more. The first electrolytic solution 407 contains carbon dioxide (dissolved therein). The concentration of the carbon dioxide contained in the first electrolytic solution 407 is not particularly limited. Desirably, the first electrolytic solution 407 containing carbon dioxide dissolved therein is acidic.

Any material can be used for the cathode electrode 401 as long as reduction of carbon dioxide can take place at that cathode electrode, but a metal electrode is usually used. It is particularly desirable to use a metallic material containing copper (Cu) or indium (In) as a main component in view of the reaction products obtained through reduction of carbon dioxide. The cathode electrode 401 may consist of a metallic material, but may have a laminated structure of a metallic material layer and a substrate for supporting the metallic material layer. For example, the cathode electrode 401 may have a structure including a substrate such as glass or glassy carbon (registered trademark) and a thin film of a specific metallic material formed on the substrate, or a structure including a conductive substrate and a large number of fine particles of a metallic material supported on the substrate. The structure of the cathode electrode 401 is not limited as long as the cathode electrode 401 has the capability of reducing carbon dioxide. Only a part of the cathode electrode 401 may be immersed in the first electrolytic solution 407 as long as the material of the cathode electrode 401 is in contact with the first electrolytic solution 407.

A second electrolytic solution 408 is contained in the anode chamber 405, and the anode chamber 405 contains an anode electrode 404. The anode electrode 404 is a photoelectrode that exhibits its activity when irradiated with light. The anode electrode 404 includes a region including a nitride semiconductor in which an aluminum gallium nitride layer and a gallium nitride layer are laminated. As the anode electrode 404, for example, the anode electrode 10a or the like as described above is used. The anode electrode 404 is in contact with the second electrolytic solution 408. Specifically, the anode electrode 404 is immersed in the second electrolytic solution 408.

The second electrolytic solution 408 contained in the anode chamber is, for example, an aqueous sodium hydroxide solution (aqueous NaOH solution). The concentration of the second electrolytic solution is desirably 1 mol/L or more, and particularly desirably about 5 mol/L. Desirably, the second electrolytic solution 408 is basic.

As described later, the region of the anode electrode 404 (photoelectrode) immersed in the second electrolytic solution 408 is irradiated with light having a wavelength of at least 360 nm or less from a light source 403.

In order to separate the first electrolytic solution 407 from the second electrolytic solution 408, the proton conducting membrane 406 is interposed between the cathode chamber 402 and the anode chamber 405. This means that the first electrolytic solution 407 and the second electrolytic solution 408 are not mixed together.

The proton conducting membrane 406 is not particularly limited as long as it allows protons to pass therethrough but prevents other substances from passing therethrough. An example of the proton conducting membrane 406 is Nafion (Registered Trademark).

The cathode electrode 401 and the anode electrode 404 have electrode terminals 410 and 411, respectively. These electrode terminals 410 and 411 are electrically connected to each other by a conducting wire 412 without an external power source such as a battery, a solar cell, or a potentiostat provided therebetween. That is, the cathode electrode 401 is electrically connected to the anode electrode 404 through the conducting wire.

(Method for Reducing Carbon Dioxide by Light Energy)

Next, the method for reducing carbon oxide using the above-described device is described.

A carbon dioxide reduction device 400 can be placed at room temperature and under atmospheric pressure.

As shown in FIG. 4, the photoelectrode (anode electrode) 404 is irradiated with light from the light source 403. An example of the light source 403 is a xenon lamp. The light from the light source 403 has a wavelength of 360 nm or less. Particularly desirably, the light has a wavelength of 250 nm or more and 325 nm or less.

Desirably, the device includes a gas inlet tube 409, as shown in FIG. 4. In the carbon dioxide reduction process, it is desirable to reduce carbon dioxide contained in the first electrolytic solution 407 while supplying carbon dioxide into the first electrolytic solution 407 through the gas inlet tube 409. One end of the gas inlet tube 409 is immersed in the first electrolytic solution 407. It is also desirable to supply carbon dioxide into the first electrolytic solution 407 through the gas inlet tube 409 so as to dissolve a sufficient amount of carbon dioxide in the first electrolytic solution 407 before starting the reduction of carbon dioxide.

In the case where the cathode electrode 401 contains an appropriate metallic material, carbon dioxide contained in the first electrolytic solution 407 is reduced by irradiating the photoelectrode (anode electrode) 404 with light so as to produce formic acid, carbon monoxide, hydrocarbon, alcohol, aldehyde, etc.

EXAMPLES

The present disclosure is described in more detail with reference to the following examples.

Example 1

As a conductive substrate, a low-resistance single-crystalline gallium nitride substrate (a GaN substrate with a thickness of about 0.4 mm and a diameter of about 50 mm) was used. On the substrate, an n-type, low-resistance gallium nitride thin film doped with silicon (with a film thickness of 2.0 μm and a Si doping level of $2.5 \times 10^{18}$ cm$^{-3}$), an undoped second aluminum gallium nitride thin film (composition formula: $Al_yGa_{1-y}N$, with an aluminum composition ratio (the value of y) of $0 \leq y \leq 0.11$ and a thickness of 100 nm), and an undoped first aluminum gallium nitride thin film (composition formula: $Al_xGa_{1-x}N$, with an aluminum composition ratio (the value of x) of x=0.11 and a thickness of 100 nm) were epitaxially grown in this order by metal-organic vapor-phase epitaxy. The composition ratio of Al (the value of y) in the second aluminum gallium nitride layer was changed continuously so that the value of y was 0 at the interface with the gallium nitride layer and 0.11 at the interface with the first aluminum gallium nitride layer, as shown in FIG. 3A. Furthermore, a large number of nickel oxide fine particles (with a size of several tens of nanometers to several micrometers) were arranged in a distributed manner on the first aluminum gallium nitride layer of the photoelectrode by solution reaction. Then, an electrode layer (with a thickness of about 500 nm) containing titanium (Ti), aluminum (Al), and gold (Au) was formed on the back surface of the GaN substrate. Thus, the photoelectrode (anode electrode) 404 used for carbon dioxide reduction, as shown in FIG. 1D, including the conductive substrate, the n-type gallium nitride layer formed on the conductive substrate, the second aluminum gallium nitride layer formed on the n-type gallium nitride layer, the first aluminum gallium nitride layer formed on the second aluminum gallium nitride layer, and nickel oxide fine particles arranged on the surface of the first aluminum gallium nitride layer so as to coat a part of the surface, was obtained.

As the cathode electrode 401, a copper plate (Cu plate) with a thickness of 0.5 mm was used. The Cu plate used as the cathode electrode was subjected to treatment for removing an oxide film formed on the surface or etching so as to form a clean copper surface before use. About 4 cm$^2$ of the Cu plate was immersed in the first electrolytic solution.

A carbon dioxide reduction device shown in FIG. 4 was fabricated using the photoelectrode (anode electrode) and the cathode electrode prepared as described above. The distance between the photoelectrode (anode electrode) and the cathode electrode was about 8 cm. The specific configuration of the device was as follows.

First electrolytic solution 407: aqueous potassium bicarbonate solution (aqueous $KHCO_3$ solution in an amount of 180 mL) with a concentration of 3.0 mol/L Second electrolytic solution 408: aqueous sodium hydroxide solution (aqueous NaOH solution in an amount of 180 mL) with a concentration of 5.0 mol/L Proton conducting membrane 406: Nafion membrane "Nafion 117" (DuPont)

Light source 403: xenon lamp (with rated power of 300 W, a light irradiation area of about 4 cm$^2$, and an irradiation light power of about 20 mW/cm$^2$)

Carbon dioxide was supplied into the device by bubbling carbon dioxide gas (at a flow rate of 200 mL/min) in the first electrolytic solution 407 for 30 minutes through the gas inlet tube 409. The anode chamber 405 includes a light irradiation window (not shown), and through the light irradiation window, the surface of the photoelectrode (anode electrode) was irradiated with light having a wavelength of 360 nm or less from the light source 403 for a given period of time.

Comparative Example 1

A carbon dioxide reduction device was fabricated using the same photoelectrode (anode electrode) and the same copper cathode electrode as those in Example 1, except that the second aluminum gallium nitride layer was not formed and the first aluminum gallium nitride layer was formed directly on the gallium nitride layer.

The photoelectrode (anode electrode) 404 in the device configured in this manner was irradiated with light from a light source. As a result, in both Example 1 and Comparative Example 1, reaction currents (in an amount of 6 to 12 mA) flowed through the conducting wires. When light irradiation was stopped, no reaction current was observed. This means that some sort of reactions occurred at the photoelectrode and the cathode electrode by light irradiation.

In view of the above, the present inventors have further studied these reactions in detail in the following manner. Specifically, after the cathode chamber filled with a specific amount of carbon dioxide and the anode chamber filled with argon gas were sealed, the photoelectrode (anode electrode) was irradiated with light for a specific period of time (1 to 3 hours). Then, the gas components and the reaction products generated in the cathode chamber and the anode chamber by the activities of the cathode electrode and the anode electrode were identified and the amounts of these components and products were measured. The gas components were analyzed by gas chromatography. Liquid components were analyzed by liquid chromatography and head-space gas chromatography. Furthermore, the amount of electric charge (in coulombs) associated with the carbon dioxide reduction reaction was calculated from the integrated value of the amount of reaction current obtained by the light irradiation.

As a result, in both Example 1 and Comparative Example 1, it was confirmed that, as carbon dioxide reduction products, carbon monoxide (CO), formic acid (HCOOH), etc. were produced in the cathode chamber in which the cathode electrode was placed. The amount of each of these reaction products varied in proportion to the amount of electric charge (in coulombs) associated with the reaction. It was confirmed from these results that light irradiation of only the photoelectrode caused the cathode electrode (copper electrode) to develop a catalytic reaction to reduce carbon dioxide. The total amount of the reaction products generated through carbon dioxide reduction in Example 1 was larger by 10 to 20% than that in Comparative Example 1.

On the other hand, in the anode chamber in which the photoelectrode (anode electrode) was placed, oxygen ($O_2$) in an amount corresponding to the amount of the reaction products generated in the cathode chamber was evolved through water oxidation reaction. In addition, in Comparative Example 1, hydrogen ($H_2$) in an amount about 30 times that in Example 1 was evolved. Table 1 shows the results of the relative comparison between the amount of hydrogen evolved in the anode chamber in Example 1 and that in Comparative Example 1. Table 1 also shows the ratio of carriers supplied to the cathode electrode obtained by calculation. As used herein, the ratio of carriers supplied to the cathode electrode means the ratio of carriers (electrons) used for carbon dioxide reduction at the cathode electrode without being consumed in the photoelectrode (anode electrode) to electrons generated in the anode electrode.

TABLE 1

|  | Amount of hydrogen evolved in anode chamber (relative value) | Ratio of carriers supplied to cathode electrode (%) |
|---|---|---|
| Example 1 | 0.033 | 99.3 |
| Com. Example 1 | 1.000 | 82.1 |

These results reveal that in both Example 1 and Comparative Example 1, carriers were generated by light irradiation of the photoelectrode (anode electrode) and carbon dioxide reduction reaction occurred at the cathode electrode, but in Example 1, almost all the carriers generated in the anode electrode were supplied to the cathode electrode without being used to produce hydrogen, that is, without being lost, whereas in Comparative Example 1, some of the carriers generated in the anode electrode were consumed for producing hydrogen at the anode electrode (in the anode chamber) without being transferred to the cathode electrode. The ratio of the lost carriers was about 20%.

Presumably, in Comparative Example 1, the amount of electrons supplied to the cathode electrode decreased due to the loss of electrons, resulting in a decrease in the amount of reaction products obtained by carbon dioxide reduction. As described above, in Example 1 where the second aluminum gallium nitride layer for promoting transport of carriers in the photoelectrode was interposed, the efficiency of carbon dioxide reduction was improved.

Example 2

A photoelectrode configured as shown in FIG. 1A was prepared without arranging nickel oxide fine particles on the surface of the first aluminum gallium nitride layer, and experiments were conducted using this photoelectrode in the same manner as in Example 1.

As a result, it was confirmed that no hydrogen was produced in the anode chamber and that the same reaction products as those in Example 1 were obtained as carbon dioxide reduction products.

Example 3

Experiments were conducted using the same photoelectrode as that used in Example 1 except that the distribution of the Al composition ratio in the second aluminum gallium nitride layer of the photoelectrode was changed step by step (FIG. 3B) instead of being changed continuously (FIG. 3A).

As a result, it was confirmed that hydrogen was not evolved at the photoelectrode (in the anode chamber) and almost the same reaction products as those in Example 1 were obtained by carbon dioxide reduction.

Example 4

Figure 2A:
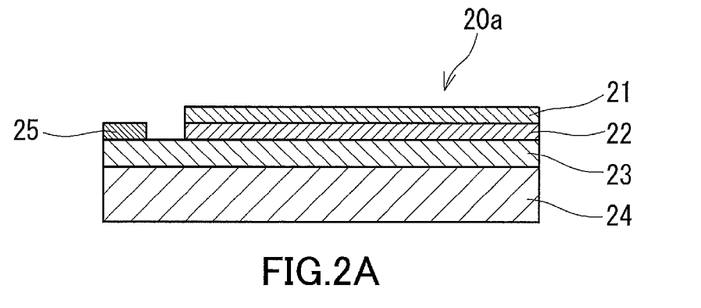
FIG. 2A to FIG. 2D are each a schematic view showing another example of the structure of a photoelectrode (anode electrode) used for carbon dioxide reduction according to the present disclosure.
Figure 2B:
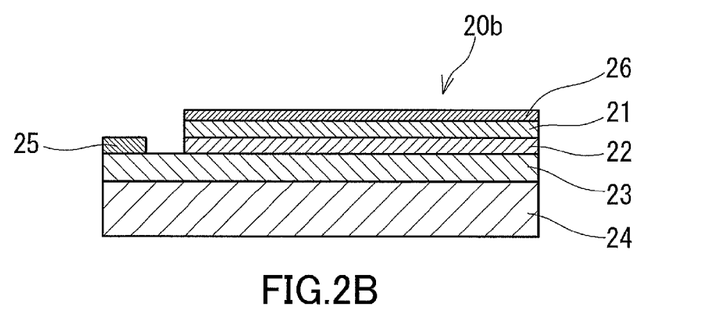
Figure 2C:
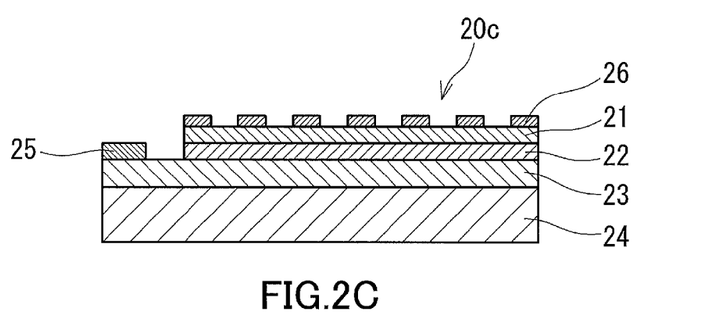
Figure 2D:
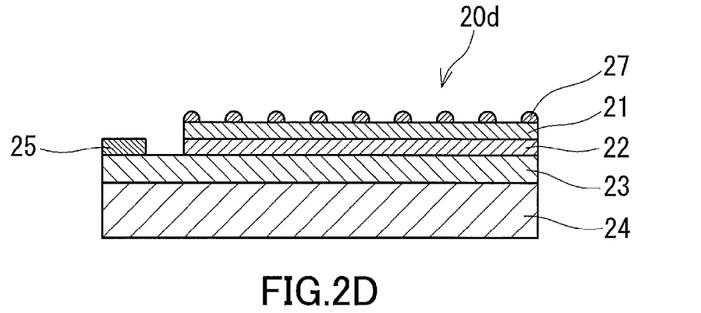

Experiments were conducted in the same manner as in Example 1 except that a single-crystalline sapphire substrate was used as a substrate on which a nitride semiconductor layer was to be formed and an epitaxial growth process was used to form a photoelectrode configured as shown in FIG. 2D.

As a result, it was confirmed that hydrogen was not evolved at the photoelectrode (in the anode chamber) and almost the same reaction products as those in Example 1 were obtained by carbon dioxide reduction.

Example 5

Experiments were conducted in the same manner as in Example 1 except that a glassy carbon (registered trademark) substrate with a large number of copper fine particles supported on the surface thereof was used instead of a copper plate as a cathode electrode.

As a result, it was confirmed that hydrogen was not evolved at the photoelectrode (in the anode chamber) and almost the same reaction products as those in Example 1 were obtained by carbon dioxide reduction. In addition, almost the same result was obtained when a copper-nickel alloy containing traces of nickel component was used instead of copper fine particles.

Example 6

Experiments were conducted in the same manner as in Example 1 except that an indium plate was used instead of a copper plate as a cathode electrode.

As a result, it was confirmed that hydrogen was not evolved at the photoelectrode (in the anode chamber) but most of the reaction products obtained by carbon dioxide reduction was formic acid, which means that formic acid was produced selectively.

Example 7

Experiments were conducted in the same manner as in Example 1 except that an aqueous potassium chloride solution (aqueous KCl solution) was used as a first electrolytic solution contained in the cathode chamber.

As a result, it was confirmed that hydrogen was not evolved at the photoelectrode (in the anode chamber) but the reaction products obtained by carbon dioxide reduction included alcohols such as ethylene ($C_2H_4$) and ethanol ($C_2H_5OH$) and aldehyde components in addition to carbon monoxide (CO) and formic acid (HCOOH). The same results were obtained when an aqueous sodium chloride (NaCl) solution was used as a first electrolytic solution.

Example 8

Experiments were conducted in the same manner as in Example 1 except that the composition ratio of Al (the value of x) in the first aluminum gallium nitride layer was changed from x=0.11 to x=0.22 and that the composition ratio of Al (the value of y) in the second aluminum gallium nitride layer was continuously decreased from y=0.22 at the interface with the first aluminum gallium nitride layer toward y=0 at the interface with the gallium nitride layer.

As a result, even when the composition ratio of Al in the first aluminum gallium nitride layer was changed, hydrogen was not evolved at the photoelectrode (in the anode chamber) and the same reaction products as those in Example 1 were obtained by carbon dioxide reduction.

As described above, it was confirmed that, in a light energy-driven carbon dioxide reduction device including a combination of a novel photoelectrode (anode electrode) containing a nitride semiconductor and a cathode electrode capable of reducing carbon dioxide, the loss of excited carriers generated (the production of hydrogen) at the photoelectrode (in the anode chamber) is suppressed and carbon dioxide is reduced efficiently by light energy alone in the cathode chamber. This novel photoelectrode (anode electrode) serving as an oxygen producing electrode includes a nitride semiconductor region in which a first aluminum gallium nitride layer (composition formula: $Al_xGa_{1-x}N$ (0<x≤0.25), where x is a fixed value), a second aluminum gallium nitride layer (composition formula: $Al_yGa_{1-y}N$ (0≤y≤x), where y is a variable value), and a gallium nitride layer are laminated.

The present disclosure may be embodied in other forms without departing from the spirit or essential characteristics thereof. The embodiments disclosed in this specification are to be considered in all respects as illustrative and not limiting. The scope of the present disclosure is indicated by the appended claims rather than by the foregoing description, and all changes which come within the meaning and range of equivalency of the claims are intended to be embraced therein.

INDUSTRIAL APPLICABILITY

The present disclosure provides a photoelectrode used to reduce carbon dioxide by light energy. The present disclosure also provides a method for reducing carbon dioxide using this photoelectrode.

The invention derived from the above disclosure is as follows.

A method for reducing carbon dioxide using a carbon dioxide reduction device, the method including the steps of:
(a) preparing the carbon dioxide reduction device including a cathode chamber, an anode chamber, a proton conducting membrane, a cathode electrode, and an anode electrode, wherein
a first electrolytic solution is contained in the cathode chamber,
a second electrolytic solution is contained in the anode chamber,
the cathode electrode is in contact with the first electrolytic solution,
the anode electrode is in contact with the second electrolytic solution,
the proton conducting membrane is interposed between the cathode chamber and the anode chamber,
the first electrolytic solution contains carbon dioxide,
the cathode electrode is electrically connected to the anode electrode,
a power source that is electrically connected to the cathode electrode and the anode electrode is not provided between the cathode electrode and the anode electrode;
the anode electrode includes a nitride semiconductor layer,
the nitride semiconductor layer includes an $Al_xGa_{1-x}N$ layer (0<x≤0.25), an $Al_yGa_{1-y}N$ layer (0≤y≤x), and a GaN layer,
the $Al_yGa_{1-y}N$ layer is interposed between the $Al_xGa_{1-x}N$ layer and the GaN layer,
a value of x is fixed in a thickness direction of the $Al_xGa_{1-x}N$ layer,
a value of y decreases from an interface with the $Al_xGa_{1-x}N$ layer toward an interface with the GaN layer, and
the $Al_xGa_{1-x}N$ layer is electrically connected to the cathode electrode through the $Al_yGa_{1-y}N$ layer and the GaN layer; and
(b) irradiating the $Al_xGa_{1-x}N$ layer with light having a wavelength of 360 nanometers or less so as to reduce, at the cathode electrode, the carbon dioxide contained in the first electrolytic solution.

What is claimed is:
1. A photoelectrode used to reduce carbon dioxide by light energy, comprising a region including a nitride semiconductor layer in which a first aluminum gallium nitride layer, composition formula of which is $Al_xGa_{1-x}N$, where a value of x representing a composition ratio of Al is a fixed value that satisfies 0<x≤0.25, a second aluminum gallium nitride layer, composition formula of which is $Al_yGa_{1-y}N$, where a value of y representing a composition ratio of Al is a variable value that satisfies 0≤y≤x, and a gallium nitride layer, composition formula of which is GaN, are laminated in this order from a surface of the photoelectrode to be irradiated with light, wherein
the value of y in the second aluminum gallium nitride layer changes, without any increase, from an interface with the first aluminum gallium nitride layer toward an interface with the gallium nitride layer.

2. The photoelectrode according to claim 1, wherein the value of x in the first aluminum gallium nitride layer of the photoelectrode is in a range of 0.05≤x≤0.15.

3. The photoelectrode according to claim 1, wherein the gallium nitride layer of the photoelectrode is n-type or $n^+$-type.

4. The photoelectrode according to claim 1, wherein an entire surface or a part of the surface of the first aluminum gallium nitride layer of the photoelectrode is coated with at least nickel oxide.

5. The photoelectrode according to claim 4, wherein the nickel oxide is in the form of fine particles.

6. A method for reducing carbon dioxide by light energy, the method comprising the steps of:
(a) preparing a carbon dioxide reduction device including a cathode chamber, an anode chamber, a proton conducting membrane, a cathode electrode, and an anode electrode, wherein the anode electrode is a photoelectrode that includes a region including a nitride semiconductor layer in which a first aluminum gallium nitride layer, composition formula of which is $Al_xGa_{1-x}N$, where a value of x representing a composition ratio of Al is a fixed value that satisfies $0<x\leq0.25$, a second aluminum gallium nitride layer, composition formula of which is $Al_yGa_{1-y}N$, where a value of y representing a composition ratio of Al is a variable value that satisfies $0\leq y\leq x$, and a gallium nitride layer, composition formula of which is GaN, are laminated in this order from a surface of the photoelectrode to be irradiated with light, wherein the value of y in the second aluminum gallium nitride layer changes, without any increase, from an interface with the first aluminum gallium nitride layer toward an interface with the gallium nitride layer, a first electrolytic solution is contained in the cathode chamber, a second electrolytic solution is contained in the anode chamber, the cathode electrode is in contact with the first electrolytic solution, the anode electrode is in contact with the second electrolytic solution, the proton conducting membrane is interposed between the cathode chamber and the anode chamber, the first electrolytic solution contains carbon dioxide, the cathode electrode is electrically connected to the anode electrode, and a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution.

7. The method according to claim 6, wherein the cathode electrode is a metal electrode.

8. The method according to claim 7, wherein the cathode electrode as the metal electrode contains copper or a copper compound.

9. The method according to claim 7, wherein the cathode electrode as the metal electrode contains indium or an indium compound.

10. The method according to claim 6, wherein the first electrolytic solution is an aqueous potassium bicarbonate solution.

11. The method according to claim 6, wherein the first electrolytic solution is an aqueous potassium chloride solution or an aqueous sodium chloride solution.

12. The method according to claim 6, wherein the second electrolytic solution is an aqueous sodium hydroxide solution.

13. The method according to claim 6, wherein in the step (b), the carbon dioxide reduction device is placed at room temperature and under atmospheric pressure.

14. The method according to claim 6, wherein in the step (b), at least one of alcohol, aldehyde, formic acid, carbon monoxide, and hydrocarbon is obtained from the carbon dioxide.

* * * * *